(12) United States Patent
Traversaz et al.

(10) Patent No.: US 9,377,015 B2
(45) Date of Patent: Jun. 28, 2016

(54) TUBE PUMP, TUBE CLAMP, PERFUSION SET AND SYSTEM COMPRISING A TUBE PUMP AND A TUBE CLAMP

(71) Applicant: Fresenius Vial SAS, Brezins (FR)

(72) Inventors: Philippe Traversaz, Saint-Blaise du Buis (FR); Damien Archat, Grenoble (FR)

(73) Assignee: Fresenius Vial SAS, Brezins (FR)

( * ) Notice: Subject to any disclaimer, the term of this patent is extended or adjusted under 35 U.S.C. 154(b) by 0 days.

(21) Appl. No.: 14/351,595

(22) PCT Filed: Nov. 1, 2012

(86) PCT No.: PCT/EP2012/071643
§ 371 (c)(1),
(2) Date: Apr. 14, 2014

(87) PCT Pub. No.: WO2013/072199
PCT Pub. Date: May 23, 2013

(65) Prior Publication Data
US 2014/0234144 A1    Aug. 21, 2014

Related U.S. Application Data

(60) Provisional application No. 61/560,317, filed on Nov. 16, 2011.

(30) Foreign Application Priority Data

Nov. 16, 2011    (EP) .................................... 11189354

(51) Int. Cl.
*A61M 39/28*    (2006.01)
*F04B 43/12*    (2006.01)

(52) U.S. Cl.
CPC ............ *F04B 43/1223* (2013.01); *A61M 39/28* (2013.01); *A61M 39/284* (2013.01)

(58) Field of Classification Search
CPC .............. A61M 39/28–39/287; F04B 43/1223
See application file for complete search history.

(56) References Cited

U.S. PATENT DOCUMENTS 5,290,239 A     3/1994  Classey et al.
5,423,769 A  *  6/1995  Jonkman et al. .............. 604/250
(Continued)

FOREIGN PATENT DOCUMENTS

WO      WO 93/05829      4/1993
WO      WO 2004/007015   1/2004
WO      WO 2011/119425   9/2011

OTHER PUBLICATIONS

Written Opinion dated Jan. 23, 2013, for International Application No. PCT/EP2012/071643.
(Continued)

*Primary Examiner* — Nathan R Price
*Assistant Examiner* — Melissa A Snyder
(74) *Attorney, Agent, or Firm* — Cook Alex Ltd.

(57) ABSTRACT

The invention concerns a tube pump comprising a cradle (1) with a cavity (11) suitable for the accommodation of a tube clamp (2). It further concerns a tube clamp (2) for a flexible tube, the tube clamp being suitable for accommodation in a tube pump, the tube clamp having a mobile part and an immobile part (20) designed to penetrate at least partly into a housing (11) realized in the tube pump. The invention also concerns a perfusion set. Finally, the invention concerns a system comprising a tube pump and a tube clamp. In order to provide a system comprising a tube pump and a tube clamp with improved operation safety, the tube pump has a cavity (11) with at least one protrusion (14) and the tube clamp (2) has means (21) for snapping attachment of the tube clamp behind the protrusion (14). This arrangement allows to fix the tube clamp (2) safely in the cavity (11) and to give furthermore a feedback to the user because he feels (and he might in addition hear) that the tube clamp has snapped behind the protrusion. A further advantage resides in the fact that the solution according to the present invention can be put in place without significantly increasing the costs of the parts involved in the invention.

7 Claims, 3 Drawing Sheets

(56) References Cited

U.S. PATENT DOCUMENTS

Figure 1:
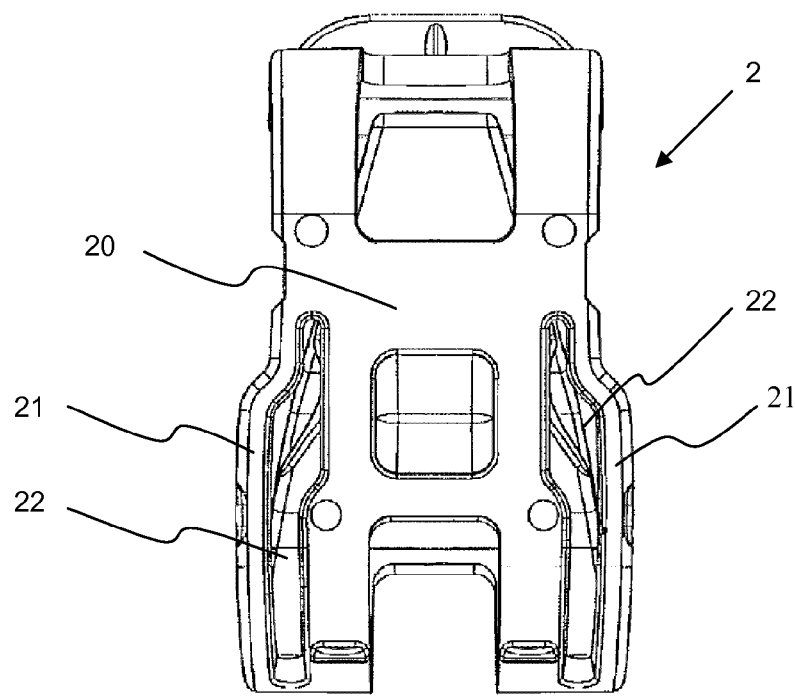

| | | | |
|---|---|---|---|
| 8,465,464 B2 * | 6/2013 | Travis | A61M 39/28 604/250 |
| 8,469,933 B2 * | 6/2013 | Zhang et al. | 604/250 |
| 2010/0268161 A1 | 10/2010 | Traversaz | |

OTHER PUBLICATIONS

International Search Report dated Jan. 23, 2013, for International Application No. PCT/EP2012/071643.

International Preliminary Report on Patentability dated Oct. 21, 2013, for International Application No. PCT/EP2012/071643.

* cited by examiner

TUBE PUMP, TUBE CLAMP, PERFUSION SET AND SYSTEM COMPRISING A TUBE PUMP AND A TUBE CLAMP

The invention concerns a tube pump comprising a cradle with a cavity suitable for the accommodation of a tube clamp. It further concerns a tube clamp for a flexible tube, the tube clamp being suitable for accommodation in a tube pump, the tube clamp having a mobile part and an immobile part designed to penetrate at least partly into a housing realized in the tube pump. The invention also concerns a perfusion set. Finally, the invention concerns a system comprising a tube pump and a tube clamp.

Document WO 2009/030625 A1 describes a clamp for a flexible tube, composed of a substantially U-shaped plastic band, the free end of the first branch of the U being bent over, so as to form the head of the clamp, to the free end of the second branch, called the back, in such a way that, in the closed position, the free end of the back is situated resting under the free end of the head, whereas, in the opened position, the free end of the back is situated at a distance above the free end of the head, the clamp having a pair of openings to allow a flexible tube to extend through the clamp and be supported by the latter, and two opposite projections for closing the flexible tube by compressing it when the clamp is in the closed position. The document also relates to a pump provided with means for opening a clamp.

The document U.S. Pat. No. 4,689,043 A concerns an intravenous tube activator for use with a peristaltic intravenous pump which comprises means that require the closure of a tube associated clamp upon engagement of the intravenous tube with the pump and upon any subsequent disengagement of the intravenous tube from the pump. The activator further comprises means which simultaneously move the tube associated clamp to open the intravenous tube when the pump is being operated.

An arrangement for coupling an intravenous hose having a roller clamp with an infusion pump is described in EP 1 616 588 A1. A hose clamp has clamping surfaces in the form of legs which can move relative one another about a hinge, the legs being enveloped on their outside by a biased clamping spring, and the device is formed by an expander rib that is fastened to the inside of the door and can be brought into engagement with the legs of the hose clamp so to produce the open position after closing the door to expand the legs. The housing has a receiver, into which the hose clamp can be snapped and a locking device is present in the housing that prevents the closing of the door if the hose clamp is not inserted into the receiver and permits the closing of the door when the hose clamp is fully inserted.

U.S. Pat. No. 4,372,304 A concerns a flow control system for accurately controlling the rate and total quantity of a fluid being delivered intravenously to a patient and a restrictor for use therein. A microprocessor provides control signals to a stepping motor which, through appropriate gearing, causes movement of a plunger so as to increase or decrease the compression of a plastic tube of an intravenous set which is captured in a disposable adapter mounted in registration with the plunger.

The object of the present invention is to provide a tube pump which allows safe operation. It is another object of the invention to improve tube clamps for use with such tube pumps. A further object of the invention is to provide a perfusion set or a system comprising a tube pump and a tube clamp with improved operation safety.

This object is achieved concerning the tube pump according to the invention in that the cavity comprises at least one protrusion allowing to secure the tube clamp snapped behind the protrusion(s).

This arrangement allows to fix the tube clamp safely in the cavity and to give furthermore a feedback to the user because he feels (and he might in addition hear) that the tube clamp has snapped behind the protrusion. A further advantage resides in the fact that the solution according to the present invention can be put in place without significantly increasing the costs of the parts involved in the invention.

In a preferred embodiment of the invention, the cavity comprises two protrusions.

In this case, the protrusions are preferably facing each other.

In another embodiment of the invention, the cavity comprises a bottom and at least one wall area perpendicular or essentially perpendicular to the bottom, the at least one protrusion being preferably located at the at least one wall area.

The at least one protrusion may have any form, but it is preferred that the at least one protrusion is in the form of a cylinder, the extremity of which is preferably curved or chamfered.

In a preferred embodiment of the invention the tube pump is a medical tube pump, preferably a peristaltic medical tube pump.

Concerning the tube clamp, the object of the invention is achieved in that the tube clamp comprises means for snapping attachment of the tube clamp to the tube pump.

According to a preferred embodiment of the invention, the means for snapping attachment are located on the immobile part of the tube clamp.

Preferably, the means for snapping attachment comprise at least one bar-shaped element which is elastically deformable by lateral pressure.

Optionally, the means for snapping attachment comprise two bar-shaped elements which are preferably located on the opposite each other.

Preferably, the means for snapping attachment are located on the tube clamp in such a way that the main part of their projection on the plane perpendicular to the introduction direction of the tube clamp into the cavity is situated at the outside of the projection of the part of the tube clamp penetrating deeply into the cavity as the means for snapping attachment.

A perfusion set comprising a tube clamp according to the invention and a flexible tube is also within the scope of the invention.

As far as a system comprising a tube pump and a tube clamp or a perfusion set is concerned, the object of the invention is achieved in that the means for snapping attachment of the tube clamp are suitable for interacting with the at least one lateral protrusion of the tube pump.

Figure 2:
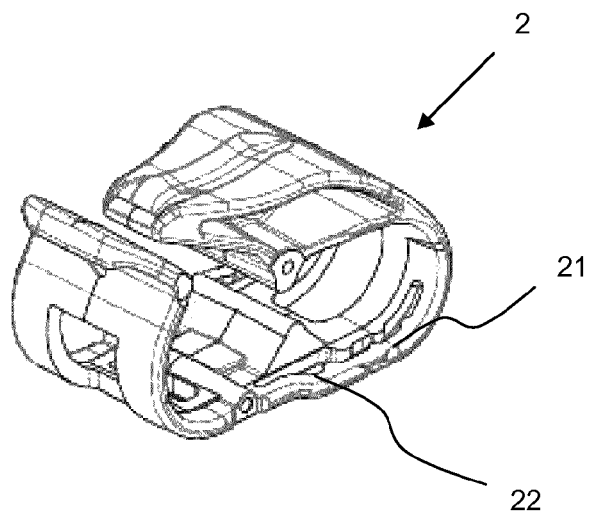
Figure 3:
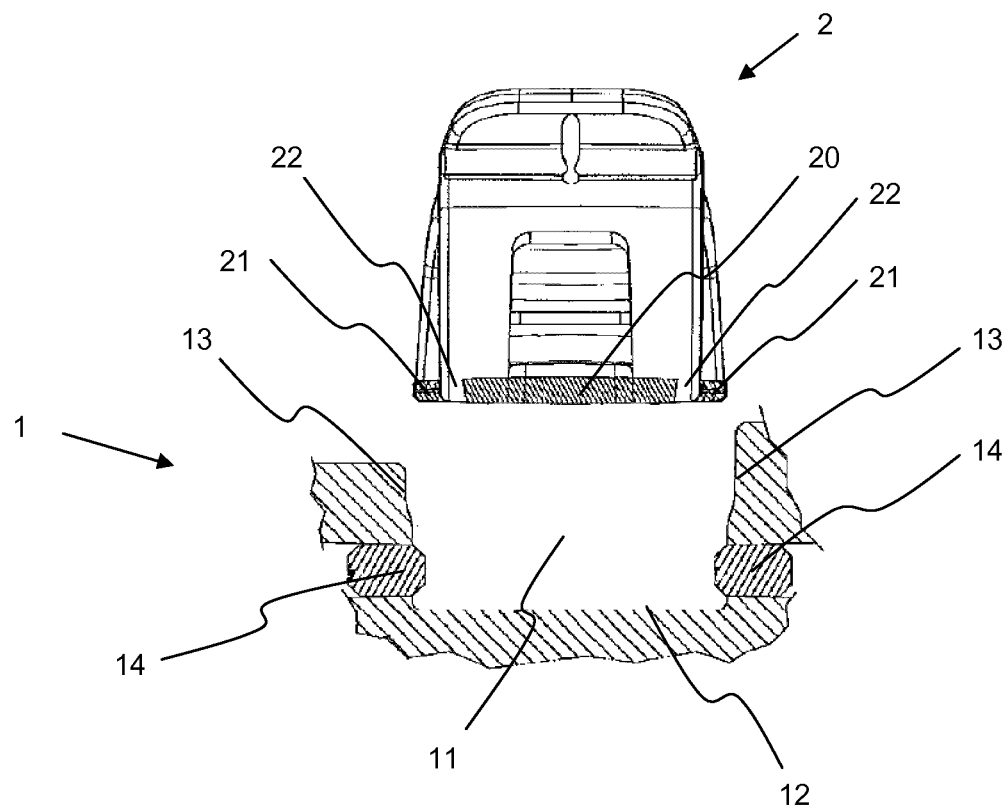
Figure 4:
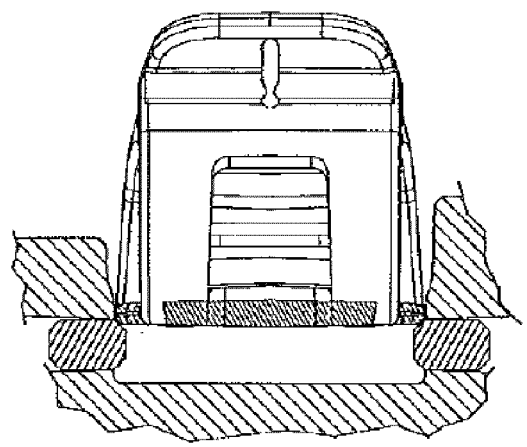
Figure 5:
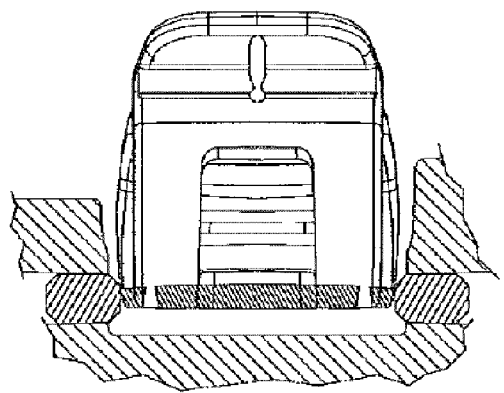
Figure 6:
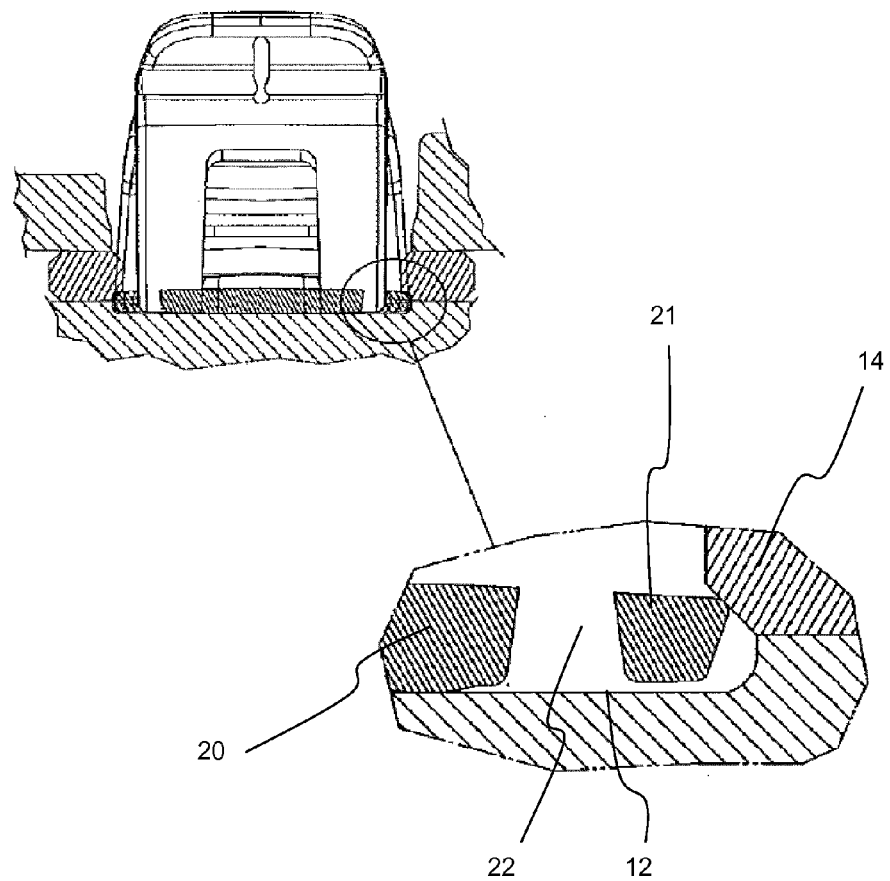

The invention will be discussed in the following with reference to the drawings in which FIG. 1 shows a bottom view of a tube clamp according to the invention, FIG. 2 shows a perspective view of a tube clamp according to the invention, FIG. 3 shows a tube clamp before entering into the cavity of the tube pump, FIG. 4 shows the tube clamp upon entry into the cavity of the tube pump, FIG. 5 shows the tube clamp after having reached the protrusions of the cavity, FIG. 6 shows the tube clamp snapped behind the protrusions.

The tube clamp (2) shown in the figures is a tube clamp of the <<snail>> type. Generally, its form is essentially U-like. The lower branch (20) of the U is designed to be received in a cavity (11) of complementary form which is realized in the clamp cradle (1) of a pump. This lower branch (20) remains immobile once the tube clamp (2) is placed in the cavity (11), whereas the upper branch is mobile with respect to the lower branch (20) and the cavity (11) between a closed position in which it exercises pressure on the tube in order to squeeze it and an open position in which it does not exercise pressure on the tube.

As shown in FIG. 1, the tube clamp (2) according to the invention is provided with means (21) for snapping attachment of the tube clamp (2) to a tube pump, preferably a medical tube pump. These means (21) are located on the tube clamp (2) in a such a way that the main part of their projection on the plane perpendicular to the introduction direction of the tube clamp (2) into the cavity (11) is situated at the outside of the projection of the part of the tube clamp (2) penetrating deeply into the cavity (11) as the means (21) for snapping attachment. In the example shown here, these means (21) are placed in the plane of the lower branch (20), distant from its lateral edges.

The means for snapping attachment of the tube clamp (2) to a tube pump comprise at least one bar-shaped element (21) extending along the outside of the lower part of the tube clamp (2). In the shown example, there are two lateral bar-shaped elements (21) placed symmetrically on each side of the tube clamp (2). The bar-shaped elements (21) are in the shown example an integral part of the tube clamp (2). They are linked to the tube clamp (2) only on their extremities and laterally separated from the main body of the tube clamp (2) by openings (22). Due to the elasticity of the material of the bar-shaped elements (21) (which is generally also the material of the tube clamp (2)) and to the lateral opening (22), the bar-shaped elements (21) are elastically deformable by lateral pressure.

The FIGS. 3 to 6 show in a sequence the different steps of insertion of such a tube clamp (2) into a cavity (11) provided in a cradle (1) of a tube pump.

As shown in FIG. 3, the tube clamp (2) is placed over the cavity (11) provided in a cradle (1) of a tube pump, preferably a peristaltic tube pump. This cavity (11) of the shown example comprises a bottom (12) and two side wall areas (13) perpendicular to the bottom (12) or slightly inclined with respect to the perpendicular to the bottom (12). The side wall areas (13) are provided each with a protrusion (14) allowing to secure the tube clamp (2) snapped behind the protrusion (14). As shown in the example, the protrusions (14) are facing each other. These protrusions (14) are in the form of cylinders fixed in housings in such a way that their extremities extent into the cavity (11). These extremities are preferably curved or chamfered.

FIG. 4 shows the next step of the insertion of the tube clamp (3) into the cavity (11). The tube clamp (2) has entered the cavity (11) insofar as the bar-shaped elements (21) touch the upper part of the protrusions (14).

If further pressure is exerted onto the top of the tube clamp (2), as shown in FIG. 5, the protrusions (14) exert in reaction a lateral pressure onto the bar-shaped elements (21) of the tube clamp (2) which bend elastically towards the lower centre of the tube clamp (2).

FIG. 6 shows the final situation in which the bar-shaped elements (21) of the tube clamp (2) are snapped behind the protrusions (14) thereby securing the tube clamp (2) in the cavity (11). A detail view shows that in this position the bar-shaped elements (21) due to their elasticity have at least partially returned to their initial position in which no lateral pressure is exerted on them.

At the moment when the bar-shaped elements (21) return into their previous state, the typical snapping noise alerts the user about the fact that the tube clamp (2) is now securely fixed in the cavity (11).

As the extremities of the protrusions (14) are curved or chamfered, it is possible to pull the tube clamp (2) out of the cavity (11) when this is required. The extracting operation is inversed to the described insertion operation.

It is worthwhile to mention that the means (21) for snapping attachment could be located elsewhere than in the plane of the lower branch (20) of the pump.

Despite the fact that the example shows a tube clamp of the "snail" type, the invention is also applicable to any other type of tube clamps, e.g. to a "slide clamp", of which a part is placed in a cavity and remains immobile in it during the functioning of the pump.

The invention claimed is:

1. A system comprising a tube clamp for a flexible tube and tube pump having a clamp cradle for removably receiving the tube clamp;

the tube clamp further comprising:
 a base generally defining a plane and having first and second lateral edges;
 first and second elongated bar-shaped elements, each having opposed ends formed integrally with the lateral edges of the base so as to define an elongated opening between each bar-shaped element and its associated lateral edge, the opposed ends of each bar-shaped element connecting to the base, each bar-shaped element being deformable toward and away from its associated lateral edge in response to application of lateral force in the plane of the base;

the clamp cradle further comprising:
 a cavity having a closed periphery and a bottom with a sidewall extending generally perpendicularly between the periphery and the bottom to define an opening having a shape complementary to the base of the tube clamp so that the tube clamp is received in the cavity when the plane of the base is oriented parallel to the bottom of the cavity and the tube clamp is moved substantially perpendicularly to the base, the sidewall having an inward protrusion adjacent the bottom of the cavity for engaging the bar-shaped elements to deform the bar-shaped elements inwardly for insertion and removal of the tube clamp from the cavity for snapping attachment of the tube clamp to the clamp cradle.

2. The system according to claim 1 wherein the cavity comprises two protrusions.

3. The system according to claim 2 wherein the protrusions are facing each other.

4. The system according to claim 1 wherein the protrusion is in the form of a cylinder having a curved or chamfered upper and lower surface.

5. The system according to claim 1 wherein the tube pump is a peristaltic medical tube pump.

6. A tube clamp for a flexible tube comprising:
 an upper branch and a lower branch defining a generally U-shape;
 the lower branch comprising a base generally defining a plane and having first and second lateral edges;
 first and second elongated bar-shaped elements, each having opposed ends formed integrally with the lateral edges of the base so as to define an elongated opening between each bar-shaped element and its associated lateral edge, the opposed ends of each bar-shaped element connecting to the base, each bar-shaped element being deformable toward and away from its associated lateral edge in response to application of lateral force in the plane of the base.

7. A perfusion set comprising a tube clamp according to claim 6 and a flexible tube.

\* \* \* \* \*